United States Patent [19]

Hollenberg et al.

[11] Patent Number: 4,835,258

[45] Date of Patent: May 30, 1989

[54] CONJUGATION OF AROMATIC AMINES OR NITRO-CONTAINING COMPOUNDS WITH PROTEINS OR POLYPEPTIDES BY PHOTOIRRADIATION OF THE AZIDE DERIVATIVES WITH ULTRAVIOLET LIGHT IN ORDER TO PRODUCE ANTIBODIES AGAINST THE HAPTENS

[75] Inventors: Paul F. Hollenberg, Skokie; Ramendra N. Pandey, Lombard, both of Ill.

[73] Assignee: Northwestern University, Evanston, Ill.

[21] Appl. No.: 946,436

[22] Filed: Dec. 24, 1986

[51] Int. Cl.$^4$ .............................. C07K 7/00
[52] U.S. Cl. ................... 530/391; 530/389; 530/402; 530/403; 530/405; 530/409; 530/807; 530/810; 530/812; 530/816; 435/174; 435/177; 435/188; 204/157.68; 204/157.6; 204/157.67
[58] Field of Search ............. 530/389, 391, 402, 403, 530/405, 409, 807, 810, 812, 816; 435/174, 177, 188; 204/157.68, 157.6, 157.67

[56] References Cited

U.S. PATENT DOCUMENTS

| 3,492,212 | 1/1970 | Searcy .................. 204/157.68 |
| 3,867,269 | 2/1975 | Shimonishi et al. ........ 204/157.68 |
| 4,275,000 | 6/1981 | Ross ...................... 435/188 |
| 4,625,014 | 11/1986 | Senter et al. .............. 404/88 |

FOREIGN PATENT DOCUMENTS 8601720  3/1986  PCT Int'l Appl. ............. 424/85

OTHER PUBLICATIONS

Pandey et al, *J. Immunol. Methods* 94, 1986, pp. 237–46.

*Primary Examiner*—Delbert R. Phillips
*Assistant Examiner*—Garnette D. Draper
*Attorney, Agent, or Firm*—Tilton, Fallon, Lungmus and Chestnut

[57] ABSTRACT

A method of linking primary aromatic amine- or nitro-compounds to carrier proteins by photochemical reactions in order to produce antibodies against the haptens.

13 Claims, No Drawings

CONJUGATION OF AROMATIC AMINES OR NITRO-CONTAINING COMPOUNDS WITH PROTEINS OR POLYPEPTIDES BY PHOTOIRRADIATION OF THE AZIDE DERIVATIVES WITH ULTRAVIOLET LIGHT IN ORDER TO PRODUCE ANTIBODIES AGAINST THE HAPTENS

REFERENCE TO GRANT

This invention was developed pursuant to Grant CA-16954 awarded by the National Cancer Institute.

BACKGROUND OF THE INVENTION

This invention relates to a method of linking primary aromatic amines to carrier proteins by photochemical reactions in order to produce antibodies against the amine haptens.

More specifically, the invention relates to a method for coupling aromatic nitro- or amine-containing drugs or other compounds to carrier proteins for the purpose of raising antibodies against the coupled compound. The conjugated proteins can then be used to produce antibodies specific for the coupled haptenic group or, if the drugs are coupled to antibodies, these may then be used to increase the efficacy of drug delivery to targeted sites and decrease toxicity. The coupling reaction is rapid and occurs under mild conditions which do not result in denaturation or loss of function of the carrier proteins. The coupling procedure provides for high labeling densities which can be obtained without loss of protein function.

Two methods are primarily used to conjugate primary aromatic amines to carrier proteins. They are the diazocoupling method (Inman, et al., 1973, *Immunochem.* 10, 153-163) and the isocyanate method (Spragg, et al., 1966, *J. Immunol.* 96, 865-871). However, there are some disadvantages to the use of these methods. The conjugated proteins prepared by these methods may sometimes fail to elicit an anti-hapten antibody response, which may be attributed to the highly alkaline conditions required for coupling. It is also difficult to prevent side reactions associated with diazonium coupling, which may result in extensive precipitation. Furthermore, the bonds formed by the diazonium salts are easily cleaved. Finally, the extent of the diazocoupling is mainly dependent on the presence of tyrosine and histidine residues in the carrier protein, which further restricts the applicability of this approach. The isocyanate method of Creech, H. J. (1952) *Cancer Res.*, 12, 557-564 has been used for conjugating carcinogenic aromatic primary amines to carrier proteins. This method involves the derivatization of the primary aromatic amine to form the isocyanate followed by coupling to the Σ-amino group of a lysine residue. Fraenkel-Conrat, H. L. (1944) *J. Biol. Chem.* 152, 385-389 reported that isocyanates react with the —SH groups of cysteine and Miller, et al. (1941) *J. Biol. Chem.* 141, 905-920 have reported that isocyanates also react with —OH groups of tyrosine. However, Creech, et al. (1941) *J. Am. Chem. Soc.* 63, 1670-1673 were unable to conjugate zein with isocyanates even under favorable experimental conditions. Additionally, attempts by Creech et al. (1941) *J. Am. Chem. Soc.* 63, 1661-1669 to increase the epitope density (the number of haptenic groups attached per molecule carrier) beyond a certain level resulted in denaturation of the protein. The coupling conditions for this method, stirring the hapten and carrier protein at alkaline pH and 4° C. overnight, are similar to those for the diazocoupling method and present the same problems. The specific functional group requirements of the isocyanate coupling procedure also restrict the applicability of this method.

Photolabeling techniques have previously not been used to conjugate primary aromatic amines with carrier proteins in order to elicit antibodies against the hapten. Primary aromatic amines may be easily derivatized to azido compounds which are reasonably stable in the dark and at low temperatures. The resultant azido derivatives are photolabile when irradiated with ultraviolet (UV) light in ethanolic or aqueous solutions, giving rise to highly reactive nitrene radicals which can undergo insertion reactions.

There is a need to conjugate aromatic nitro- or amine-containing compounds to carrier proteins in a relatively short period of time at physiological pH.

SUMMARY OF THE INVENTION

The present invention is directed to a novel approach for raising antibodies against aromatic nitro- or amine-containing drugs, carcinogens, carbohydrates, or other compounds by using photolabeling methods to produce hapten-carrier conjugates. The conjugation to carrier proteins involves mild reaction conditions which do not result in denaturation or loss of function of the carrier protein and which results in high labelling densities. These conjugates can then can be used in the production of antibodies against the conjugated haptens. These antibodies could be used for monitoring drug levels in body fluids using RIA or ELISA methods. Further, the antibodies could also be used to estimate the amounts of drugs, chemical carcinogens, and other xenobiotics bound to deoxyribonucleic acid (DNA), ribonucleic acid (RNA) or protein so that levels of these adducts could be determined in any tissue of interest. Additionally, the coupling process can be utilized to improve the efficacy of drug delivery to target tissues. For example, chemotherapeutic agents, radiolabeled compounds, etc. can be conjugated to polyclonal or monoclonal antibodies against tumor-specific antigens and these can then be used to target the conjugated compounds for delivery to the appropriate target tissue (i.e., in this case, the tumor). This method of selective targeting could lead to a marked improvement of therapeutic efficacy with a significant decrease in general toxicity.

Briefly, aromatic nitro compounds may be reduced to give the aromatic amine. The amine can then be converted to the azido compound by diazotization with nitrous acid followed by treatment with sodium azide. Aromatic azides can also be produced by various other synthetic routes such as displacement of halide ion by azide. The aromatic azide can then be conjugated to a protein or polypeptide by irradiation with ultraviolet light. The aryl azides are photolabile and upon photolysis give rise to highly reactive nitrene radicals which can then undergo insertion reactions with the amino acid side chains on proteins or polypeptides to form covalent adducts. The conjugated protein can then be separated from the unbound photolysis products by gel exclusion chromatography and the conjugated protein can then be used for antibody production against the conjugated aromatic compound, or delivery of a drug conjugated to the protein, etc.

Therefore, it is an object of the present invention to provide a method for the production of antibodies against a specific hapten.

It is another object of the present invention to provide a drug delivery system.

DETAILED DESCRIPTION OF THE INVENTION

The photolysis of aryl azides is well known. The use of nitrene insertion in the case of most biological molecules will result in a wide range of undefined linkage positions on the molecule. Although the spectrum of linkages may be reduced somewhat by electrostatic or other interactions, there should be, in most cases, a large number of possible coupling sites. Probability considerations alone dictate that coupling at most of these sites will have little if any effect on the biological activity of the macromolecule. Some of these insertion sites on proteins are C=S, C—H, C=O, S—H, or N—H bonds. Under proper conditions, all proteins can be labeled by using nitrene insertion since the functional residues required for insertion of nitrenes are routinely found in the backbones of all proteins. The structure of the linkage region between hapten and carrier protein would be R—N=N-carrier for azo coupling, R—N-H—CO—NH-carrier for the isocyanate method, and R—NH-carrier for the photolabeling method. The linkage bond obtained by photolabeling is more similar to the parent amine, resulting in the production of antibodies of greater specificity for the haptenic group.

The method of the present invention is applicable to the coupling of any nitro- or amino-containing compounds to a protein or polypeptide. The carrier protein influences the antibody response to a hapten. Due to the general nature of the photolabeling method, it is possible to study the effectiveness of various carriers in eliciting antibody response either with different proteins conjugated to similar extents or for determining optimum epitope density for antibody response by using the same protein with varying epitope densities. In accordance with the present invention, even at high epitope densities, the protein carriers are not denatured in contrast to conventional procedures where high epitope densities appear to lead to denaturation of the carrier molecule. Examples of carrier proteins and peptides that can be utilized in the present invention include bovine serum albumin (BSA), human transferrin (TR), thyroglobulin (TH), poly (lysine.tyrosine), and poly (lysine.phenylalanine). This listing is not intended to be limiting, for any protein or peptide may be used in the process of the present invention such as various protein components isolated from human and animal serum tissue and cellular extracts and protein components from pathogenic parasites. The conjugation of the azido analog of the nitro- or amino-containing compound to the carrier protein by photoirradiation generally occurs in about 1 second to thirty minutes at physiological pH. Preferably, the pH may range from about 6.8 to about 7.8. Irridation may be by ultraviolet or visible light for about 1 second to about thirty minutes. The conjugated protein can be purified by conventional techniques and isolated in about 2 to about 3 hours.

Typically, aryl azides are conjugated to bovine serum albumin using standard photolabeling procedures. After photolysis, the conjugated protein is separated from the unbound photolysis products of the aryl azide on a gel exclusion column. The following examples illustrate a preferred embodiment of the present invention but are not to be construed as a limitation thereon.

EXAMPLE I

Hapten Carrier Conjugation

A 24 ml. volume of a 500 µg/ml solution of bovine serum albumin (BSA) in 100 mM potassium phosphate buffer, pH 7.4, was stirred at 4° C. in a 50 ml beaker. To this solution, 1.0 ml of 5 mM 3-azido-N-ethylcarbazole (ANEC) in ethanol was added and the sample was photoirradiated for 6 minutes from the top by placing a UVP model B-100A long UV lamp at a distance of 6 cm as measured from the bottom of the beaker. The photolyzed sample was passed through a Sephadex G-10 column (4×0.8 cm) and equilibrated with 100 mM potassium phosphate, pH 7.4. The protein containing fraction from the column was reprocessed using the same sequence (addition of 1.0 ml of 5 mM ANEC dissolved in ethanol, photolysis for 6 minutes, and chromatography on a Sephadex G-10 column) 3 more times. After the last photolysis and gel filtration on the Sephadex G-10 column, the proteins containing eluate was used for injection of rabbits as described in Example II. Hapten-thyroglobulin (TH) and hapten-human transferrin (TR) conjugates were also prepared in the same way. For labeling the poly (Lys.HBr, Tyr) 1:1, and the poly(Lys.HBr, Phe) 1:1, 500 µg/ml solutions of the polypeptides were made in distilled water and the conjugations carried out as previously described.

Labeling

ANEC was photolyzed in 100 mM potassium phosphate buffer, pH 7.4, in the absence of protein and passed through a Sephadex G-10 column. The photolyzed ANEC remained at the top of the column and did not elute, even after washing the column with 50 column volumes of 15% ethanol in 100 mM phosphate buffer, pH 7.4. When the column was washed with 95% ethanol, the photolyzed ANEC eluted quantitatively as a yellow band. In order to estimate the number of ANEC groups bound to the carrier proteins, this observation was utilized. The Sephadex G-10 column used to separate the unbound ANEC and photolysis products from protein-bound ANEC, was first washed with 10 column volumes of 15% ethanol in 100 mM phosphate buffer, pH 7.4. The washing buffer was then changed to 95% ethanol and the unbound photolysis products of ANEC eluted. The 95% ethanol eluate was flash evaporated and the residue weighed. The differences between the total amount of ANEC added in four cycles and the residue which eluted from the column gave an approximation of the amount of ANEC bound to the carrier protein. Calculations for this procedure are given in Table 1.

TABLE 1

| Carrier Protein | Amount of ANEC Recovered (µmoles) from G-10 Column | Amount Bound to Carrier Protein (µmoles) | Epitope Density | Epitope Density per 1000 daltons |
| --- | --- | --- | --- | --- |
| BSA | 4.6 | 15.4 (77)[b] | 85 | 1.28 |

TABLE 1-continued

| Carrier Protein | Amount of ANEC Recovered (μmoles) from G-10 Column | Amount Bound to Carrier Protein (μmoles) | Epitope Density | Epitope Density per 1000 daltons |
|---|---|---|---|---|
| Transferrin | 4.0 | 16.0 (80) | 107 | 1.33 |
| Thyroglobulin | 5.6 | 14.4 (72) | 800 | 1.20 |
| Poly Lys—Phe | 5.0 | 15.0 (75) | 50 | 1.25 |
| Poly Lys—Tyr | 3.8 | 16.2 (81) | 120 | 1.35 |

[a]Calculated Using the following molecular weights: BSA, 66,000; Transferrin, 80,000; Thyroglobulin, 669,000; poly (Lys—Phe), 40,000; and poly (Lys—Tyr), 90,000.
[b]Percent of total ANEC bound to the carrier protein.

EXAMPLE II

Immunization Protocol

New Zealand white female rabbits weighing 1–1.5 kg were used for immunization. They were obtained from Lesser's Rabbitory, Union Grove, Wis. Preimmune sera were obtained from blood removed from the marginal ear vein of each rabbit. Each antigen (600 μg in 1.5 ml of 100 mM potassium phosphate, pH 7.4) was mixed with an equal volume of Freund's complete adjuvant and the emulsified preparation injected at multiple sites subcutaneously and intramuscularly. Three weeks after the first injection, the rabbits were bled and a booster dose (100 μg of antigen in 1.0 ml of 100 mM potassium phosphate, pH 7.4, mixed with equal amount of incomplete Freund's adjuvant) was injected in multiple subcutaneous, intramuscular and intraperitoneal sites and repeated at three to four week intervals with specimens of blood obtained 7–10 days after each series of injections. The blood specimens were allowed to clot at 4° C. and the collected serum was stored at −20° C.

Evaluation of Antisera Titers

The titers of the antisera were measured using a solid-phase, hapten-specific, non-competitive enzyme-linked immunosorbent assay (ELISA). Antigen titrations (0.01, 0.05, 0.1, 0.5, 1.0, 5.0, 10.0 and 50 μg/ml of ANEC-protein were used for coating the wells) and antisera titrations (1/500, 1/1000, 1/2,500, 1/5,000, 1/10,000, 1/15,000, 1/20,000, and 1/30,000 dilutions) were performed using Dynatech Immunolon II 96 well microtiter plates. From the linear portions of the titration curves a serum dilution of 1:1,000 and a coating antigen concentration of 1.0 μg/ml were selected for titer evaluation studies. The wells of the Immunolon II plates were coated with 200 μl of 1 μg/ml ANEC-protein conjugate in 0.1M NaHCO$_3$, pH 9.0, at ambient temperature for 2 hr., backcoated with 1% ovalbumin in PBS (0.01M sodium phosphate buffer, pH 7.3, containing 0.15M sodium chloride) for 1 hr. at ambient temperature, and then washed three times with wash buffer (1% BSA, 0.02% sodium azide, 0.1% Tween-20 in PBS, pH 7.3). Various dilutions of immune serum were made up in the wash buffer and 200 μl aliquots of each dilution added to duplicate wells. The plates were incubated at ambient temperature for 2 hr., washed three times with wash buffer and 200 μl aliquots of affinity purified IgG fraction of goat anti-rabbit IgG conjugated with β-galactosidase prepared by the method of Boraker et al. (1981 *J. Clin. Med.* 14, 396–403) were added. The plate was incubated at 4° C. overnight, washed three times with wash buffer and then freshly made substrate solution (4.0 mg/ml o-nitrophenyl-β-D-galactopyranoside, 5.0 mM MgCl$_2$, and 0.1M β-mercaptoethanol in PBS, pH 7.3) was added (200 μl). The plates were incubated for 3 hr. at ambient temperature and the optical density in each well was measured at 405 nm with a Titertek Multiskan Instrument (Flow Labs., McClean, VA).

Inhibition studies were conducted by preincubating diluted antisera (1:1000) with various concentrations of ANEC-BSA, ANEC-TH, ANEC-TR or free hapten for 2 hours prior to addition to ANEC-BSA (1 μg/ml) coated wells, with the rest of the assay being performed as described above. The percent inhibitions of antibody binding were plotted against the log of the solution phase inhibitor concentrations. In a similar manner, inhibition by the hapten, 3-amino-N-ethylcarbazole, was also investigated.

Results

Antibody responses were observed in antisera collected from two of the rabbits three weeks after the first immunization injections using the ELISA assay. The titers of the various sera were compared at 1:2000 dilution of the anti-ANEC-BSA and anti-ANEC-TR sera using ANEC-BSA coated wells (1 μg/ml coating concentration). Further immunization did not increase the titer nor did the titers decrease. The rabbit immunized with ANEC-TH conjugate failed to demonstrate anti-ANEC antibody reactivity. This response was presumed to be due to a function of the TH carrier as the other two rabbit antisera employing heterologous immunogen carriers reacted well with the ANEC-TH conjugate. Also, when this rabbit was further immunized with ANEC-TR conjugate, anti-ANEC antibodies were elicited. No other rabbits were immunized to determine whether ANEC-TH would act a as immunogen.

All of the appropriate controls in the ELISA were essentially negative. The secondary galactosidase conjugated anti-rabbit immunoglobulin reagent did not react with ANEC-conjugate coated wells and the immunoglobulins of the antisera did not react with wells which were only backcoated with ovalbumin.

The anti-ANEC-BSA serum (diluted 1:1000) was equally well inhibited by ANEC-BSA, and by the ANEC-TR and -TH conjugates. Inhibition levels of 50% were obtained for all ANEC conjugates at about 1 μM concentration calculated on the basis of the ANEC concentrations of the ANEC conjugates. Using ANEC-BSA coated wells and the anti-ANEC-TR serum, the three different ANEC carrier conjugates resulted in inhibition curves showing 50% inhibitions at a tenfold lower concentration (0.1 μM) in comparison to the anti-ANEC-BSA serum (1.0 μM concentration yielding 50% inhibition). The results indicate that the anti-ANEC-TR antibodies are of slightly higher affinity than the anti-ANEC-BSA antibodies. The ANEC-conjugates of poly-lys-phe and poly-lys-tyr also yielded similar inhibition curves. The approximately equal inhibitions obtained with the three ANEC proteins and two ANEC polypeptide conjugates (data not included) indicated that the assay conditions measured only antibodies to the ANEC haptenic group and were not apparently greatly dependent on the amino acid sequence adjacent to the ANEC adduct.

The anti ANEC-BSA sera were also inhibited by the hapten 3-amino-N-ethyl-carbazole. Inhibition of 50% was obtained at a concentration of 10 μM and 70% inhibition was observed a 1 mM concentration. The insolubility of 3-amino-N-ethyl-carbazole in aqueous buffer at concentrations above 1 mM did not allow experiments in which complete inhibition was observed.

When the anti ANEC-BSA or -TR sera were tested against BSA- or TR- coated wells, respectively, substantial antibody binding was observed demonstrating that the antisera also contained antibodies to the carriers (BSA or TR). These results indicate that the carrier proteins did not lose all their antigenicity as a result of photolabeling. The anti-BSA carrier reactivities were effectively blocked in the assays of the anti-ANEC specificity by the high concentrations of BSA in the buffer used for dilution.

The results of the foregoing examples show that the photolabeling technique of the present invention may be used to couple derivatized primary aromatic amines to carrier proteins in order to elicit an antibody response against the hapten. Further, the results illustrate the simplicity and speed with which a haptenic group can be attached to a carrier protein using the procedure of the present invention. Conventional methods, for example the diazocoupling and isocyanate methods for conjugating proteins involve alkaline pH conditions and longer reaction times for coupling, whereas the photolabeling procedure of the present invention may be carried out at physiological pH and the procedures including isolation of the conjugates can be completed in a matter of a few hours. Thus, the method of the present invention eliminates keeping the hapten and protein at alkaline pH overnight for completion of the reaction, which is one of the major disadvantages of the conventional methods. Further, the conventional methods exhibit specific functional group limitations which may be difficult to overcome. Additionally, the method of the present invention produces small amounts of waste products when compared to the diazocoupling and isocyanate coupling procedure and is therefore useful for producing antibodies against primary aromatic amine carcinogens.

It will be apparent to those skilled in the art that while only certain embodiments are set forth herein, alternative embodiments and various modifications, both of materials and methods, are apparent from the above description and examples and are considered equivalents.

What is claimed is:

1. A method of conjugating nitro or amino containing compounds to carrier proteins, without loss of function of the carrier proteins, to elicit an antibody response against the hapten wherein the improvement comprises irradiating the protein in the presence of the azido derivatives of the primary aromatic amino- or nitro-compound at physiological pH.

2. The method of claim 1 wherein the amount of time needed for the conjugation of the azido derivatives of the nitro- or amino-containing compounds to the carrier proteins is about 1 second to about 30 minutes.

3. The method of claim 1 wherein the protein conjugated can be isolated in about 2 to about 3 hours.

4. The method of claim 1 wherein the pH ranges from about 6.8 to about 7.8.

5. The method of claim 1 wherein the carrier proteins may be any protein or polypeptide.

6. The method of claim 1 wherein the carrier protein may be isolated from human or animal serum, tissue, cellular extracts or protein components of pathogenic organisms.

7. The method of claim 5 wherein the carrier protein may be selected from the group of proteins and polypeptides selected from the group consisting of bovine serum albumin, human transferrin, thyroglobulin, poly (lysine.tyrosine) and poly (lysine.phenylalanine).

8. The method of claim 1 wherein the nitro or amino containing compound may be a primary aromatic amine.

9. The method of claim 8 wherein the primary aromatic amine is converted to an azide compound.

10. The method of claim 9 wherein the azide compound is selected from the group consisting of 3-azido-N-ethyl carbazole, 1-azidopyrene, 2-azidoflourene, 2-azidonapthalene.

11. The method of claim 1 wherein the structure of the linkage region between the hapten and carrier protein is R—NH-carrier, wherein R is an aryl residue.

12. The method of claim 1 wherein the irradiation is accomplished by irradiation with ultravioloet or visible light.

13. The method of claim 1 wherein the duration of the irradiation varies from about 1 second to about 30 minutes.

* * * * *